US006441625B1

(12) United States Patent
McAllister et al.

(10) Patent No.: US 6,441,625 B1
(45) Date of Patent: Aug. 27, 2002

(54) CONTACTLESS CONDUCTIVITY DETECTOR WITH TRANSMITTER/ RECEIVER ELECTRODE

(75) Inventors: William H. McAllister, Saratoga; Byron M. Yu, San Jose, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 2 days.

(21) Appl. No.: 09/626,521

(22) Filed: Jul. 27, 2000

(51) Int. Cl.[7] ............................................... G01R 27/08
(52) U.S. Cl. ..................... 324/691; 324/226; 340/620
(58) Field of Search ................... 324/7.1, 71.4, 324/341, 442, 715, 691, 207.26, 226, 262, 326, 328, 318; 73/61.1, 61.5; 340/620; 600/13, 423

(56) References Cited

U.S. PATENT DOCUMENTS 3,944,917 A * 3/1976 Hogg ......................... 324/71.1
4,972,137 A * 11/1990 Dunstan ..................... 324/71.4
5,341,100 A * 8/1994 Taylor ........................ 324/341

OTHER PUBLICATIONS

Jose A. Fracassi da Silva & Claudimir L. do Lago "An Oscillometric Detector for Capillary Electrophoresis", *Analytical Chemistry*, vol. 70, 1998, pp. 4339–4343.
Jiri Vacik, Jiri Zuska & Iva Muselasova, "Improvement of the Performance of a High–Frequency Conductivity Detector for Isotachophoresis" Journal of Chromatography, 17,322, 1985, 5 pages.
Andress J. Zemann, Erhard Schnell, Dietmar Volger & Glnther K. Bonn, "Contactless Conductivity Detection for Capillary Electrophoresis" Analytical Chemistry, V. 70, 1998, pp. 563.567.

* cited by examiner

Primary Examiner—Michael J. Sherry
Assistant Examiner—Trung Nguyen

(57) ABSTRACT

A contactless conductivity detector uses a signal electrode arranged longitudinally between two ground electrodes. Conveniently, the ground electrodes can be integral with a metal housing that electrically shields the detector electronics from external electrical noise. The ground electrodes are defined at the locations where a capillary separation channel extends through the housing. The signal electrode is coupled to an AC transmitter through a sense resistor; the signal electrode is also coupled to a receiver that provides an output corresponding to the magnitude of the AC signal developed at the signal electrode. The signal electrode is located at a voltage-divider node between the sense resistor and the resistances of the sample fluid between the signal electrode location and the ground electrode locations. Thus, the signal developed at the signal electrode reflects the sample fluid resistance, which is the inverse of its conductivity. This single-electrode configuration provides a relatively flat response to frequency so that a single-frequency can be used for detection, as opposed to a frequency sweep, which can be required for other contactless conductivity detectors. The result is a simpler and more cost effective contactless conductivity detector suitable for use with electrophoresis and other chemical-analysis systems.

8 Claims, 5 Drawing Sheets

M1

TRANSMITTING AC SIGNAL
VIA SENSE RESISTOR
TO SIGNAL ELECTRODE
COUPLED TO GROUND ELECTRODE
VIA SEPARATION CHANNEL
ST1

GENERATING OUTPUT SIGNAL
AS A FUNCTION OF AMPLITUDE OF SIGNAL
DEVELOPED AT SIGNAL ELECTRODE
ST2

CONTACTLESS CONDUCTIVITY DETECTOR WITH TRANSMITTER/RECEIVER ELECTRODE

BACKGROUND OF THE INVENTION

The present invention relates to analytical chemistry and, more particularly, to conductivity detectors used, for example, to detect sample fluid components as they flow in a channel through a detection region. A major objective of the invention is to provide for simpler and more economical contactless conductivity detection.

Much of modern progress in the medical, environmental, forensic, and other sciences can be attributed to advances in analytical chemistry. One important class of analytical tools separates components of a sample fluid (typically, a mixture of sample components and non-sample components such as carriers, buffers, and surfactants) by moving them at different rates along a separation channel. Once the components are separated, it is usually desirable to quantify, and, perhaps, identify the components. This typically requires detection of the components. Detectors are available to monitor certain parameters, such as conductivity, fluorescence, or absorption of ultra-violet (UV) electromagnetic energy as the components pass through a detection region.

Conductivity detection is appealing for electrophoresis, in which components are separated by an electric field according to their electrophoretic mobilities. Components separated by electrophoresis necessarily have a measurable electrical conductivity associated with their electrophoretic mobilities. More generally, conductivity detection is useful for detecting the components with measurable conductivity regardless of how they arrive at the detector region.

Conductivity detection can be implemented by locating electrodes on the interior walls of an electrophoretic channel, in direct contact with the sample fluid. Typically, "transmit" (or "drive") and "receive" (or "detection") electrodes oppose each other across a transverse width or diameter of the electrophoretic channel. However; since the electrodes are in contact with the sample fluid, electrochemical reactions at the electrodes can affect both the electrodes and the sample. Such interaction can cause undesirable artifacts within a run and undermines repeatability between runs. This undesirable interaction between sample and electrodes is avoided by "contactless" conductivity detection.

Contactless conductivity detection is taught by Jose A. Fracassi da Silva & Claudimir L. do Lago "An Oscillometric Detector for Capillary Electrophoresis", *Analytical Chemistry*, vol. 70, 1998, pp. 4339–4343; Jirí Vacik, Jirí Zuska & Iva Muselasova, "Improvement of the Performance of a High-Frequency Conductivity Detector for Isotachophoresis" Journal of Chromatography, 17,322, 1985, 5 pages; Andress J. Zemann, Erhard Schnell, Dietmar Volger, & Gunther K. Bonn, "Contactless Conductivity Detection for Capillary Electrophoresis" Analytical Chemistry, V. 70, 1998, pp. 563–567. In addition, an antisynchronously driven contactless conductivity detector is the subject of commonly owned U.S. patent application Ser. No. 09/576,690 filed May 23, 2000, entitled "Sample-analysis system with anti-synchronously driven contactless conductivity detection" by Gary B. Gordon and Tom A. van de Goor.

In contactless conductivity detection, electrodes are capacitively coupled to the sample fluid through a channel wall. To this end, the electrodes can be formed on the exterior surface of the channel wall. Since the electrodes are not in contact with sample fluid, artifacts due to chemical interactions at the electrodes are eliminated and reproducibility is improved.

Since channel conductivity is measured through channel walls, detection sensitivity is an issue for contactless conductivity detectors. For many contactless conductivity detectors, sensitivity is maximal at a peak frequency, and falls off at lesser and greater frequencies. Unfortunately, the peak frequency typically varies with fluid conductivity, which is the parameter to be measured and thus is unknown. This can make the detector output difficult to interpret. Moreover, sensitivity can suffer when the detection frequency is not properly matched to the sample fluid.

The drive frequency can be swept to ensure each sample component is matched with its peak frequency. To ensure optimal detection sensitivity, the detection electronics can be tuned synchronously with the drive electronics. While this approach is workable, it adds considerably to the expense and complexity of a contactless conductivity detector. In addition, the range of the frequency sweep limits the range of conductivities that can be detected. What is needed is a simpler and more economical approach to contactless conductivity detection.

SUMMARY OF THE INVENTION

The present invention provides a contactless conductivity detector in which a "signal" electrode is used to both drive the excitation signal and sense the response. In other words, the same electrode is used for both transmission (drive) and reception (detection). One or more ground electrodes hold the sample fluid at a distance from the signal electrode at a known potential (AC ground). Drive electronics include a sense resistor and an oscillator coupled to the signal electrode through the sense resistor. Detection electronics read the signal generated at the signal electrode.

The signal electrode is the central node of a voltage divider, lying between the sense resistor and the resistance associated with the sample fluid extending between the signal electrode and the ground electrode. The AC amplitude at the voltage-divider node varies with the fluid's electrical resistance, which is the reciprocal of its conductivity. By monitoring the AC amplitude at the signal electrode, the fluid conductance can be characterized over time; thus, separated components can be detected serially as they pass a region of a fluid channel monitored by the detector.

Where a capillary tube is used for the fluid channel, there can be ground electrodes both upstream and downstream of the signal electrode. Conveniently, the ground electrodes can be monolithic (i.e., part of) the metal housing that electrically isolates the detector electronics from external electrical influences. Alternatively, ground electrodes can be fabricated on the capillary walls. In the alternative case, the housing can contact the ground electrodes. In either case, the capacitance of the ground electrodes can be very large, essentially providing an AC ground potential in the fluid channel at the frequency of operation. In addition, a more compact detector is provided for, since only one electrode (the signal electrode) need be in the interior of the housing (as opposed to two or more in the prior art).

In the case of a planer embodiment, the signal electrode, the drive electronics, and the detection electronics can be conveniently fabricated and connected on one side of the channel. Only a ground electrode and a ground connection need to be defined on the opposing side. This topology greatly simplifies manufacture of the planar detector, with concomitant economic benefits.

Serendipitously, the inventive detector provides a rather flat response to conductivity over a range of frequencies.

This means that a single drive frequency can be used throughout a sample run. The frequency sweep electronics required to optimize some prior art contactless conductivity detectors are not required. As a result, simpler and more economical conductivity detection is provided. These and other features and advantages of the invention are apparent from the description below with reference to the following drawings.

DETAILED DESCRIPTION OF THE PREFERRED EMBODIMENTS

Figure 1:
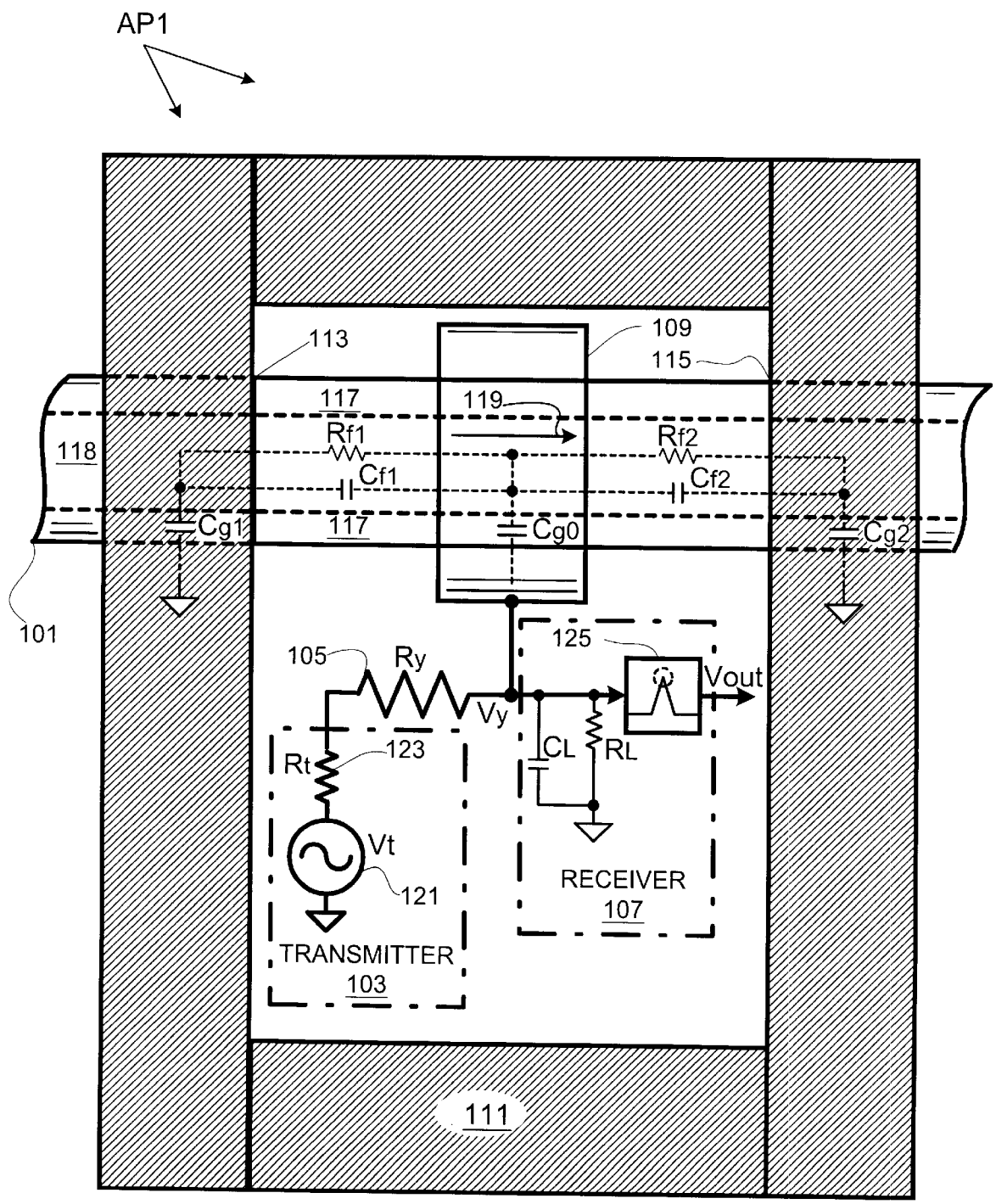
FIG. 1 is a schematic illustration of a contactless conductivity detector in accordance with the present invention.

In accordance with the present invention, a contactless conductivity detector AP1 for a capillary separation column 101 comprises a transmitter 103, a sense resistor 105, a receiver 107, a signal electrode 109, and a grounded metal housing 111, as shown in FIG. 1. Column 101 extends through housing 111; the housing metal adjacent column 101 defines a pair of ground electrodes 113 and 115. Capillary separation column 101 has a channel wall 117 that defines an interior fluid flow channel 118. The direction of migration along channel 118 is indicated by arrow 119.

Transmitter 103 includes an oscillator 121, which provides an AC voltage $v_t$. Transmitter 103 also has an inherent series resistance $R_t$, represented by resistor 123. Sense resistor 105 has an associated resistance $R_y$. Receiver 107 provides an output $V_{out}$ that is proportional to the AC magnitude of the voltage $v_y$ at signal electrode 109. Receiver 107 is shown with a peak detector 125, which is used to convert the AC signal $v_y$ to DC output $V_{out}$. In addition, receiver 107 includes an AC amplifier that provides an amplified version of signal-electrode voltage $v_y$ to peak detector 125 and a DC amplifier that amplifies the output of peak detector 125 to yield output $V_{out}$. Alternative embodiments employ different receivers with different means for detecting AC magnitude.

Electrodes 109, 113, and 115 are capacitively coupled to fluid in channel 118 through channel wall 117. Thus, a capacitance $C_{g0}$ is associated with signal electrode 119, a capacitance $C_{g1}$ is associated with ground electrode 113, and a capacitance $C_{g2}$ is associated with ground electrode 115. Capacitances $C_{g0}$ and $C_{g1}$ are electrically coupled by fluid in channel 118 between signal electrode 109 and ground electrode 113; associated with this electrical coupling are a resistance $R_{f1}$ and a capacitance $C_{f1}$ in parallel with resistance $R_{f1}$. Likewise, capacitances $C_{g0}$ and $C_{g2}$ are electrically coupled by a resistance $R_{f2}$ and a capacitance $C_{f2}$ associated with channel fluid between signal electrode 109 and ground electrode 115. Inherently, there is a load capacitance $C_L$ and a load resistance $R_L$ associated with receiver 107; load capacitance $C_L$ should be as small as possible.

Figure 2:
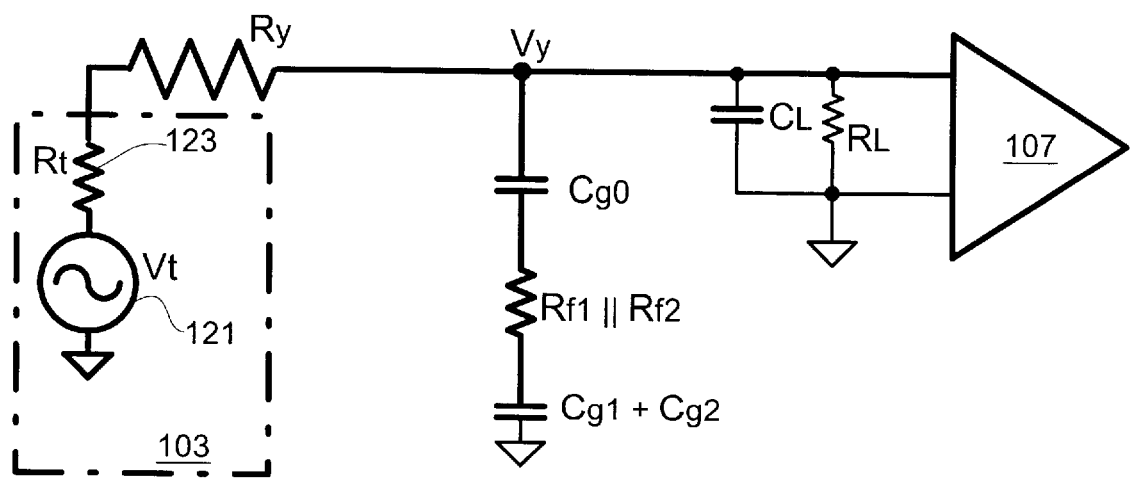
FIG. 2 is a circuit diagram showing a simplified equivalent circuit for the conductivity detector of FIG. 1.

The electrical path from oscillator 121 through resistance 123, sense resistor 105, signal electrode 109, the adjacent region of channel wall 117, the fluid in channel 118, the region of channel wall 117 at ground electrode 113, to ground electrode 113 defines a voltage divider with signal electrode 109 at the voltage-divider center node $v_y$. The voltage-divider arrangement is best shown in circuit-equivalent diagram FIG. 2, in which $R_{f1} \| R_{f2}$ is the resistance $(R_{f1}*R_{f2})/(R_{f1}+R_{f2})$ associated with parallel resistances $R_{f1}$ and $R_{f2}$. The resistance $R_t + R_y$ is constant, but the fluid resistance $R_{f1} \| R_{f2}$ varies inversely with fluid conductivity. Thus, the magnitude of voltage $v_y$ varies with sample-fluid conductivity. The same analysis applies for the parallel path from oscillator 121 to ground electrode 115.

Figure 3:
FIG. 3 is a method of the invention practicable in the context of the detector of FIG. 1.
Figure 3:

A method M1 that can be practiced using conductivity detector AP1 is flow-charted in FIG. 3. In step ST1, an AC signal is transmitted via a sense resistor to a signal electrode, where the signal electrode is coupled to a ground electrode through a separation channel. In step ST2, which is performed concurrently with step ST1, a detector output signal is generated as a function of the amplitude of the AC signal developed at the signal electrode. Of course, the method allows the signal electrode to be coupled through the separation channel to two or more ground electrodes. The ground electrodes can be part of the housing. The electrodes can be arranged longitudinally, with the signal electrode in the middle. Alternatively, the signal electrode can be disposed transversely of a ground electrode, as explained further below.

Figure 4:
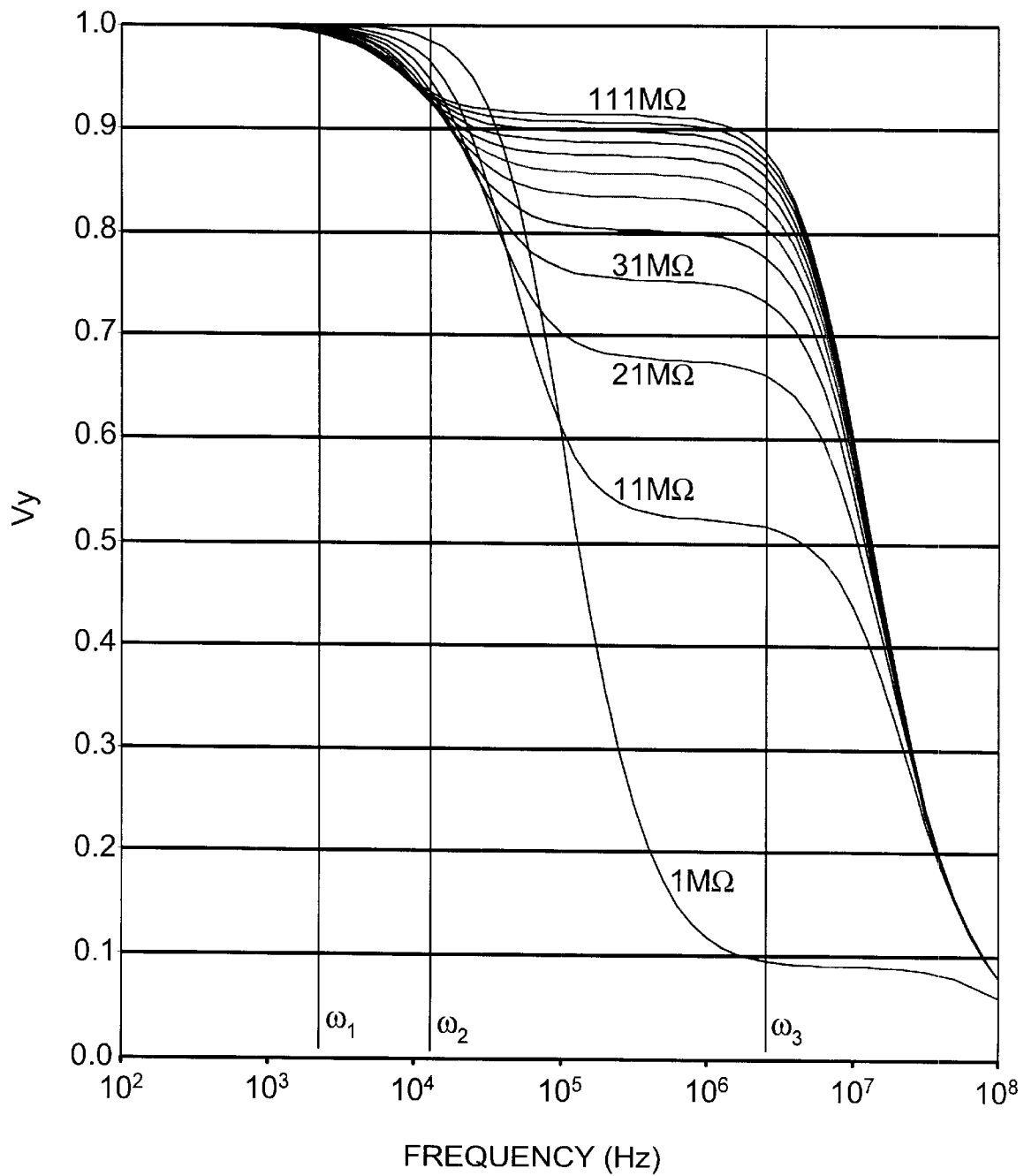
FIG. 4 is a graph of detector output as a function of frequency for a range of sample-component conductivities for the detector of FIG. 1. The conductivities are expressed as resistances from 1 MΩ to 111 MΩ in 10 MΩ increments.
Figure 5:
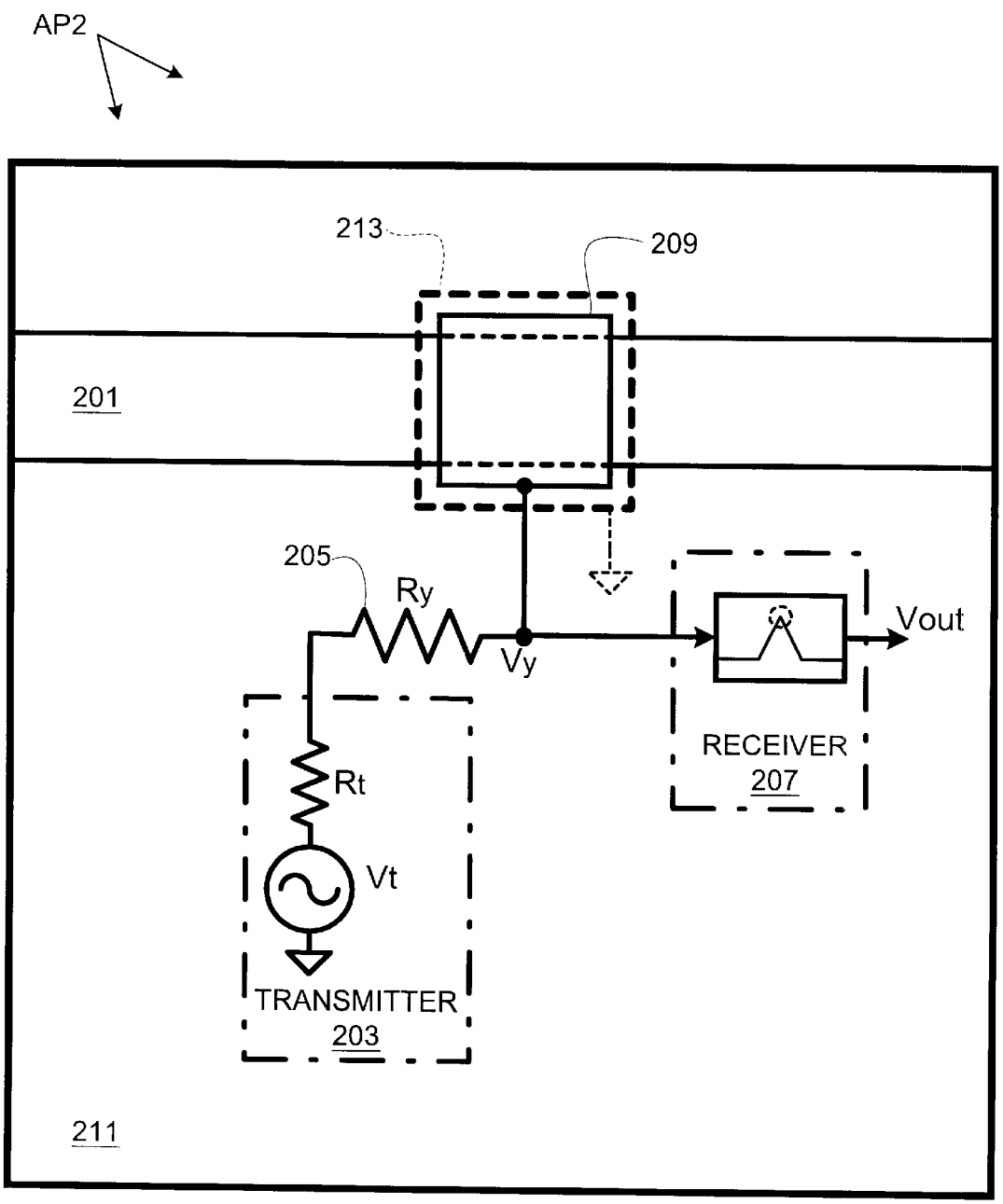
FIG. 5 is a schematic illustration of another contactless conductivity detector in accordance with the present invention and for a planar separation column.

A SPICE-generated simulation graph of output voltage versus frequency for different fluid resistivities is presented as FIG. 4. The different curves represent 10 MΩ increments of radio frequency from 1 MΩ to 111 MΩ. Note that the 11 MΩ through the 111 MΩ curves, are relatively flat between 100 kHz and 1 MHz. An AC frequency of, for example, 500 kHz could reliably distinguish different fluid conductivities. The nonflatness of the 1 MΩ curve is compensated for by its very different magnitude from the other curves.

The capacitance and resistance values used to generate the graph of FIG. 4 follow. $R_y$ is 5 MΩ; $R_t$ is 100Ω (and can thus be ignored). Capacitances $C_{f1}$, $C_{f2}$, are about 1 femtoFarads each. $C_{g1}$ and $C_{g2}$ are about 5 picoFarads (pF) each, while $C_{g0}$ is 0.4 pF. $C_L$ corresponds to the input capacitance of a modeled receiver, less than 1 pF. These values correspond to the capillary-based detector implementation. An alternative planar implementation is described further below.

Three frequency break points $\omega_1$, $\omega_2$, and $\omega_3$ are identified in FIG. 4. Ignoring $R_t$, and assuming symmetry so that $R_{f2}=R_{f1}$ and $C_{g2}=C_{g1}$, the break points can be determined using the following formulae:

$$107_1 = ((R_{f1}/2+R_y)*C_{g0})^{-1} + ((R_{f1}/2+R_y)*C_{g1})^{-1}$$

$$107_2 = (R_{f1}/2*C_{g0})^{-1} + (R_{f1}/2*C_{g1})^{-1}$$

$$107_3 = (R_y*C_L)^{-1} + (R_{f1}/2*C_L)^{-1} + (R_L*C_L)^{-1}$$

The flat region extends from $\omega_2$ to $\omega_3$. To make it larger, $\omega_2$ can be reduced, e.g., by increasing $C_{g0}$, and/or $\omega_3$ can be increased, e.g., by reducing $C_L$.

The wider the flat region, the less critical the transmission frequency. A wider flat region can be achieved by increasing the capacitance $C_{g0}$ between the fluid and the signal electrode and/or by decreasing the load capacitance $C_L$. The capillary-wall capacitance can be increased by making the signal electrode longer, but this reduces spatial resolution. Alternatively, the capillary wall can be made thinner or with a material with a higher dielectric constant or both. In practice, $C_L$ should be minimized, and $C_{g0}$ should be optimized to provide a favorable tradeoff between sensitivity and resolution. Detector API can be adjusted for maximum sensitivity for a particular range of frequencies by adjusting the value of sense resistor 105.

A second embodiment of the invention provides a detection system AP2 for a planar separation channel 201. Similar to system AP1, detection system AP2 includes a transmitter 203, a sense resistor 205, a receiver 207, and a signal electrode 209. All these components are fabricated on or in a planar polyimide assembly 211, which includes a substrate and a cover. Other materials and mechanical configurations are employed by alternative embodiments.

Separation channel 201 is etched into the substrate. A ground electrode 213 is formed on the base of the substrate and connected to ground. Transmitter 203, a sense resistor 205, a receiver 207, and a signal electrode 209 are formed on the cover for polyimide assembly 211. Note that signal electrode 209 and the single ground electrode 213 are arranged transversely with respect to separation channel 201 (as opposed to the longitudinal arrangement in detector system AP1). Otherwise, operation and performance considerations are similar.

While the foregoing embodiments involve separation channels, the invention provides for conductivity measurement irrespective of the history of the sample fluid. The invention can be used to measure the conductivity of a uniform fluid. The invention can be used to detect a series of samples that were never mixed, but instead were introduced at different times into a flowing carrier.

The present invention has industrial applicability to fields requiring chemical analysis of samples. These fields include medical, pharmaceutical, forensic and environmental sciences. These and other applications are provided for by the present invention, the scope of which is defined by the following claims.

What is claimed is:

1. A conductivity detector for a longitudinally-extending channel bearing a fluid and having a channel wall, said detector comprising:

a first ground electrode arranged for capacitive coupling to said fluid through said channel wall, said first ground electrode being held at a ground potential;

a signal electrode arranged for capacitive coupling to said fluid through said channel wall so that an electrical path from said first ground electrode to said signal electrode includes said fluid;

a receiver electrically connected to said signal electrode for providing an output as a function of a signal developed at said signal electrode;

a sense resistor electrically connected to said signal electrode; and an AC transmitter electrically coupled to said signal electrode through said sense resistor.

2. A conductivity detector as recited in claim 1 further comprising a second ground electrode held at said ground potential, said second ground electrode being arranged for capacitive coupling to said fluid through said channel wall so that an electrical path from said second ground electrode to said signal electrode includes said fluid, said signal electrode being disposed longitudinally between said first ground electrode and said second ground electrode.

3. A conductivity detector as recited in claim 2 further comprising a metal housing enclosing said signal electrode, said sense resistor, said transmitter, and said receiver, said first and second ground electrodes being monolithic with said metal housing.

4. A conductivity detector as recited in claim 1 wherein said signal electrode is spaced from said first ground electrode in a direction transverse to the longitudinal extent of said channel.

5. A method of measuring the conductivity of a fluid in a longitudinally-extending channel having a channel wall, said method comprising the steps of:

transmitting an AC waveform via a resistor to a signal electrode resistively and capacitively coupled to a ground electrode through said fluid and said channel wall; and generating an output signal as a function of the signal developed at said signal electrode.

6. A method as recited in claim 5 wherein said signal electrode is also resistively and capacitively coupled to a second ground electrode, said signal electrode being located longitudinally along said channel wall between said first ground electrode and said second ground electrode.

7. A method as recited in claim 6 wherein said first and second ground electrodes are monolithic with a housing enclosing a transmitter providing said AC waveform, said resistor, and a receiver generating said output signal.

8. A method as recited in claim 5 wherein said signal electrode is spaced from said first ground electrode along a transverse dimension orthogonal to the longitudinal extent of said channel.

* * * * *